(12) United States Patent
Zeng et al.

(10) Patent No.: US 6,500,468 B1
(45) Date of Patent: Dec. 31, 2002

(54) PANAX NOTOGINSENOSIDE COMPOSITION

(75) Inventors: Lipin Zeng, Industry, CA (US); De Pu, Industry, CA (US)

(73) Assignee: Farlong Pharmaceutical, Inc., City of Industry, CA (US)

( * ) Notice: Subject to any disclaimer, the term of this patent is extended or adjusted under 35 U.S.C. 154(b) by 0 days.

(21) Appl. No.: 10/035,258

(22) Filed: Jan. 3, 2002

(51) Int. Cl.$^7$ .......................... A61K 35/78; A61K 35/64
(52) U.S. Cl. .................... 424/728; 424/539; 514/824
(58) Field of Search ................... 424/728, 539; 514/824

(56) References Cited

FOREIGN PATENT DOCUMENTS

| CN | 1157720 | * | 8/1997 |
|---|---|---|---|
| CN | 1228960 | * | 9/1999 |
| CN | 1306839 | * | 8/2001 |
| WO | WO/9524905 | * | 9/1995 |

* cited by examiner

*Primary Examiner*—Christopher R. Tate
(74) *Attorney, Agent, or Firm*—Raymond Y. Chan; David and Raymond Patent Group

(57) ABSTRACT

A panax notoginsenoside composition for patients having coronary heart disease, high blood pressure, high blood fat, and high cholesterol, consists of 41% by weight of panax notoginsenoside powder extracted from panax notoginseng (Burk.) F. H. chen ex C. Chow et al, 0.5% by weight of beeswax, 58.48% by weight of peanut oil, and 0.02% by weight of BHT.

8 Claims, No Drawings

PANAX NOTOGINSENOSIDE COMPOSITION

FIELD OF THE PRESENT INVENTION

The present invention relates to panax notoginseng, and more particularly to a panax notoginsenoside composition consisting of panax notoginsenoside extracted from panax notoginseng.

BACKGROUND OF THE PRESENT INVENTION

According to Chinese (herbal) medicine such as Compendium of Materia Medica, panax notoginsenoside extracted from panax notoginseng can help cerebral blood vessel dilatation, increase cerebral blood flow, reduce the oxygen consumption of organism, increase the orgainism's resistance to oxygen shortage, decrease cerebrovascular resistance, enhance immune function of organism, prevent shock caused by bleeding, and provide functions of resisting thrombus, blood coagulation, and atherosclerosis.

SUMMARY OF THE PRESENT INVENTION

The main object of the present invention is to provide a panax notoginsenoside compound for patients having coronary heart disease, high blood pressure, high blood fat, and high cholesterol, which consists of 41% by weight of panax notoginsenoside powder extracted from panax notoginseng (Burk.) F. H. chen ex C. Chow et al, 0.5% by weight of beeswax, 58.48% by weight of peanut oil, and 0.02% by weight of BHT (butylated hydroxytoluene).

DETAILED DESCRIPTION OF THE PREFERRED EMBODIMENT

The present invention provides a panax notoginsenoside composition, which consists of 41% by weight of panax notoginsenoside powder, 0.5% by weight of beeswax, 58.48% by weight of peanut oil, and 0.02% by weight of BHT (butylated hydroxytoluene). The panax notoginsenoside powder, which is extracted from panax notoginseng (Burk.) F. H. chen ex C. Chow et al, comprising a compound having a chemical structure as follow:

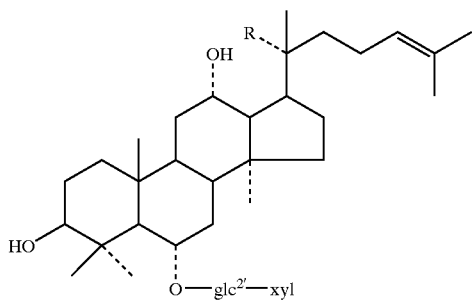

wherein R is ginsenoside and $glc^{2'}$-xyl is acetyl-ginsenoside.

The panax notoginsenoside composition of the present invention is produced by the following steps:

(1) Provide 41% by weight of panax notoginsenoside powder, 0.5% by weight of beeswax, 58.48% by weight of peanut oil, and 0.02% by weight of BHT.

(2) Dissolve the beeswax and BHT in 5% of the peanut oil under 70° C. water dissolving heat to obtain a first solution.

(3) Gradually add the panax notoginsenoside powder in the residual (95%) peanut oil under stirring until it is evenly mixed to form a second solution.

(4) Add the first solution into the second solution while stirring. Continue to stir until it is evenly mixed to form a third solution.

(5) Process the third solution through a mass-homogeneous machine to achieve a kind of thick and viscid liquid.

What is claimed is:

1. A process for producing a panax notoginsenoside composition, comprising the steps of:

(a) providing a 41% by weight of panax notoginsenoside powder, a 0.5% by weight of beeswax, a 58.48% by weight of peanut oil, and a 0.02% by weight of butylated hydroxytoluene (BHT);

(b) dissolving said beeswax and said BHT in 5% of said peanut oil when heating under a water dissolving temperature of 70°C. to obtain a first solution;

(c) gradually adding said panax notoginsenoside powder in the residual 95% of said peanut oil under continuous stirring until an evenly mixed second solution is obtained;

(d) adding said first solution into said second solution while stirring, and continuous stirring until an evenly mixed third solution is formed; and (e) forming a thick and viscid liquid that is said panax notoginsenoside composition by processing said third solution through a mass-homogeneous machine.

2. The process as recited in claim 1, wherein said panax notoginsenoside powder comprising a compound having a chemical structure of

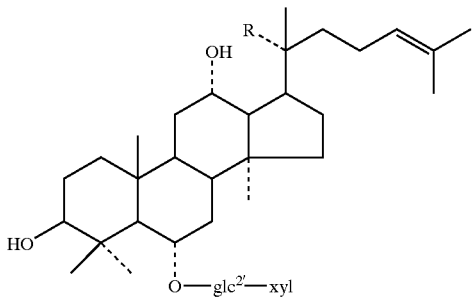

wherein said R is ginsenoside and said $glc^{2'}$-xyl is acetyl-ginsenoside.

3. The process, as recited in claim 1, wherein said panax notoginsenoside powder is extracted from a panax notoginseng.

4. The process, as recited in claim 2, wherein said panax notoginsenoside powder is extracted from a panax notoginseng.

5. A panax notoginsenoside composition produced according to a process comprising the steps of:

(a) providing a 41% by weight of panax notoginsenoside powder, a 0.5% by weight of beeswax, a 58.48% by weight of peanut oil, and a 0.02% by weight of butylated hydroxytoluene (BHT);

(b) dissolving said beeswax and said BHT in 5% of said peanut oil when heating under a water dissolving temperature of 70° C. to obtain a first solution;

(c) gradually adding said panax notoginsenoside powder in the residual 95% of said peanut oil under continuous stirring until an evenly mixed second solution is obtained;

(d) adding said first solution into said second solution while stirring, and continuous stirring until an evenly mixed third solution is formed; and (e) forming a thick and viscid liquid that is said panax notoginsenoside composition by processing said third solution through a mass-homogeneous machine.

6. The panax notoginsenoside composition, as recited in claim 5, wherein said panax notoginsenoside powder comprises a compound having a chemical structure of

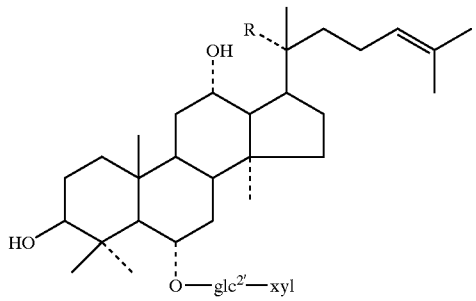

wherein said R is ginsenoside and said $glc^{2'}$-xyl is acetyl-ginsenoside.

7. The panax notoginsenoside composition, as recited in claim 5, wherein said panax notoginsenoside powder is extracted from a panax notoginseng.

8. The panax notoginsenoside composition, as recited in claim 6, wherein said panax notoginsenoside powder is extracted from a panax notoginseng.

* * * * *